(12) United States Patent
Assmus et al.

(10) Patent No.: US 10,433,896 B2
(45) Date of Patent: Oct. 8, 2019

(54) ELECTROSURGICAL GENERATOR AS WELL AS A CONTROL DEVICE AND A METHOD

(71) Applicants: OLYMPUS WINTER & IBE GMBH, Hamburg (DE); OLYMPUS CORPORATION, Tokyo (JP)

(72) Inventors: Ilja Assmus, Potsdam (DE); Yuichi Shintomi, Tokyo (JP); Koh Kawashima, Musashino (JP)

(73) Assignees: OLYMPUS WINTER & IBE GMBH, Hamburg (DE); OLYMPUS CORPORATION, Tokyo (JP)

(*) Notice: Subject to any disclaimer, the term of this patent is extended or adjusted under 35 U.S.C. 154(b) by 196 days.

(21) Appl. No.: 15/533,934

(22) PCT Filed: Jul. 16, 2015

(86) PCT No.: PCT/EP2015/066364
§ 371 (c)(1),
(2) Date: Jun. 7, 2017

(87) PCT Pub. No.: WO2016/091401
PCT Pub. Date: Jun. 16, 2016

(65) Prior Publication Data
US 2017/0325875 A1 Nov. 16, 2017

(30) Foreign Application Priority Data

Dec. 10, 2014 (DE) .................. 10 2014 225 494

(51) Int. Cl.
*A61B 18/12* (2006.01)
*A61B 18/00* (2006.01)
(Continued)

(52) U.S. Cl.
CPC .. *A61B 18/1206* (2013.01); *A61B 17/320068* (2013.01); *A61B 17/3476* (2013.01);
(Continued)

(58) Field of Classification Search
CPC .................. A61B 18/1206; A61B 2018/00666
See application file for complete search history.

(56) References Cited

U.S. PATENT DOCUMENTS

| 6,210,403 B1 | 4/2001 | Klicek |
| 6,328,703 B1 | 12/2001 | Murakami |

(Continued)

FOREIGN PATENT DOCUMENTS

| CN | 102458286 A | 5/2012 |
| CN | 102470008 A | 5/2012 |

(Continued)

OTHER PUBLICATIONS

May 22, 2018 Office Action issued in Japanese Patent Application No. 2017-530174.

(Continued)

*Primary Examiner* — Linda C Dvorak
*Assistant Examiner* — James A Cipriano
(74) *Attorney, Agent, or Firm* — Oliff PLC

(57) ABSTRACT

An electrosurgical generator, a control device, a method for operating the electrosurgical generator and a computer program product. The electrosurgical generator includes an ultrasonic generator for providing an excitation signal by which an ultrasonic converter can generate an ultrasonic vibration, a radiofrequency generator for providing a radiofrequency energy at two output contacts, and a control unit adapted to independently activate the radiofrequency generator and the ultrasonic generator. The control unit is further adapted to determine a DC-offset voltage between the two output contacts of the radiofrequency generator, check if the DC-offset voltage exceeds a DC-offset threshold value, and deactivate the ultrasonic generator if the DC-offset voltage does not exceed the DC-offset threshold.

13 Claims, 5 Drawing Sheets

(51) Int. Cl.
*A61B 17/32* (2006.01)
*A61B 17/34* (2006.01)

(52) U.S. Cl.
CPC ............... *A61B 2018/00666* (2013.01); *A61B 2018/00708* (2013.01); *A61B 2018/00875* (2013.01); *A61B 2018/00892* (2013.01); *A61B 2018/00994* (2013.01)

(56) References Cited

U.S. PATENT DOCUMENTS

| | | | |
|---|---|---|---|
| 2002/0007200 A1 | 1/2002 | Desinger | |
| 2010/0145332 A1* | 6/2010 | Shibata | A61B 17/320068 606/41 |
| 2012/0165816 A1* | 6/2012 | Kersten | A61B 17/320092 606/45 |
| 2012/0271304 A1 | 10/2012 | Werner | |

FOREIGN PATENT DOCUMENTS

| | | |
|---|---|---|
| DE | 9490465 U1 | 6/1996 |
| DE | 3942998 C2 | 11/1998 |
| DE | 100 21 529 A1 | 11/2001 |
| DE | 60314184 T2 | 1/2008 |
| DE | 10 2009 041 329 A1 | 3/2011 |
| EP | 1053719 A1 | 11/2000 |
| EP | 2353532 A1 | 8/2011 |
| EP | 2514380 A1 | 10/2012 |
| EP | 2742886 A1 | 6/2014 |
| JP | 2000-350732 A | 12/2000 |
| JP | 2012-223585 A | 11/2012 |
| WO | 2006/059067 A1 | 6/2006 |
| WO | 2010/064530 A1 | 6/2010 |
| WO | 2013/042498 A1 | 3/2013 |

OTHER PUBLICATIONS

Jul. 17, 2015 Office Action issued in German Patent Application No. 102014225494.9.
Sep. 22, 2015 Written Opinion issued in International Application No. PCT/EP2015/066364.
Sep. 22, 2015 Search Report issued in International Patent Application No. PCT/EP2015/066364.
Oct. 23, 2018 Search Report issued in Chinese Patent Application No. 201580066353.4.
Oct. 31, 2018 Office Action issued in Chinese Patent Application No. 2015800663534.

* cited by examiner

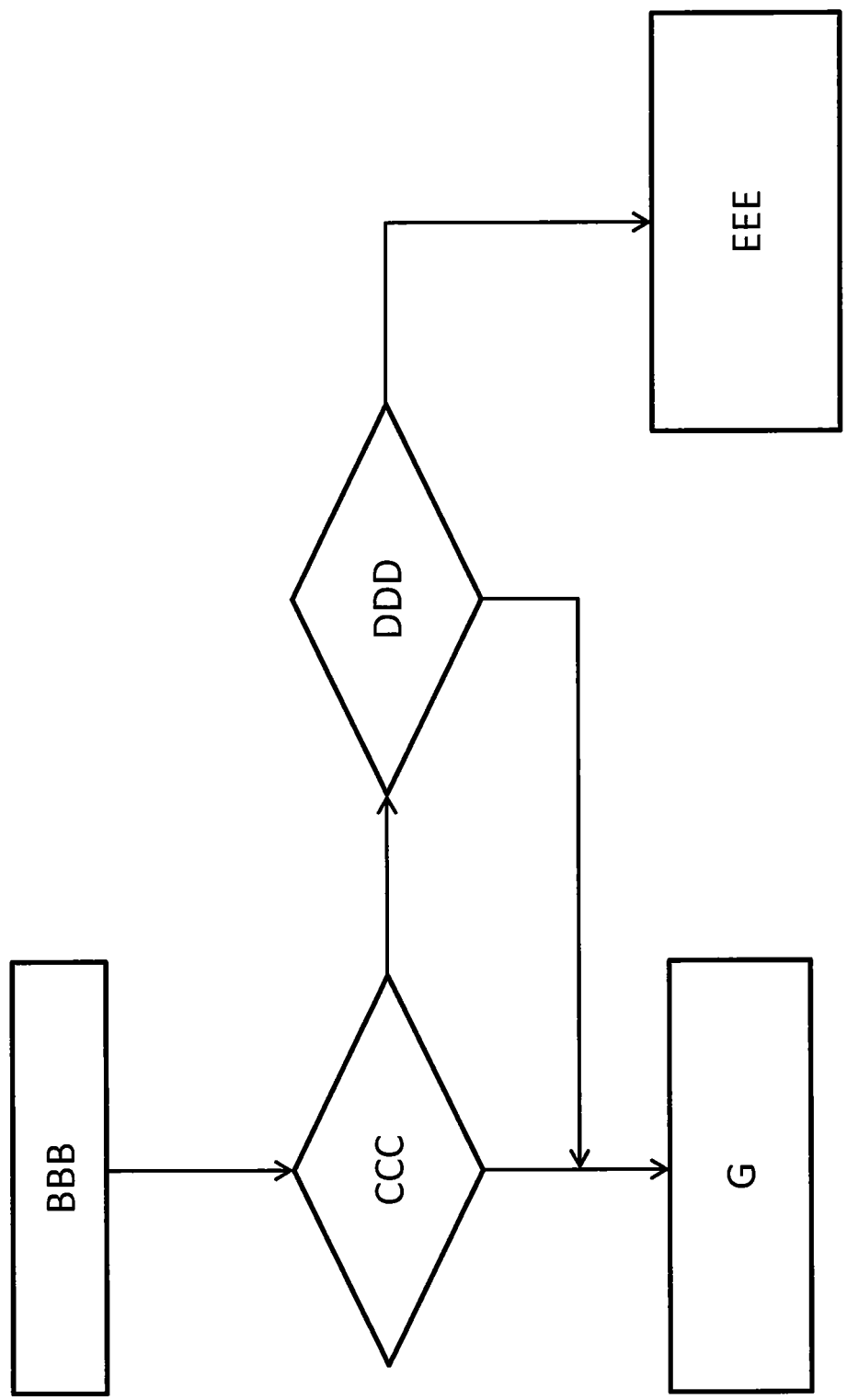

ELECTROSURGICAL GENERATOR AS WELL AS A CONTROL DEVICE AND A METHOD

The invention relates to an electrosurgical generator, comprising an ultrasonic generator for providing an excitation signal by which an ultrasonic converter can generate an ultrasonic vibration, preferably of a sonotrode of an electrosurgical instrument, a radiofrequency generator for providing a radiofrequency energy at two output contacts, preferably one of which is coupled to an electrode of the electrosurgical instrument, and a control unit adapted to independently activate the radiofrequency generator and the ultrasonic generator. The term "radiofrequency" is understood herein and in the following as electromagnetic waves in the range of radiofrequency waves. This term is equivalent to "high frequency". Therefore, both terms radiofrequency (RF) and high frequency (HF) can be used interchangeably.

The invention further relates to a control device for controlling such an electrosurgical generator, a method for operating such an electrosurgical generator as well as a computer program product.

BACKGROUND

Electrosurgical generators and electrosurgical instruments are known, for example, from DE 100 21 529 A1, U.S. Pat. No. 6,328,703 B1 and DE 10 2009 041 329 A1. In the known systems and instruments, ultrasonic vibration and RF-energy may be applied simultaneously or sequentially. Instruments for such systems are known, for example from DE 100 21 529 A1, in which an applicator can be supplied, for example, simultaneously with ultrasonic vibration and radiofrequency energy.

The existing systems and instruments provide several advantages, however further enhancements are desirable.

SUMMARY

Thus, it is an object of the present invention to provide an electrosurgical generator, a control device for such a generator, a method for controlling and/or operating such a generator as well as a computer program product, which are enhanced compared to existing generators, control devices and methods. In particular, it is an object of the present invention to provide an electrosurgical generator, a control device for such a generator, a method for controlling and/or operating such a generator as well as a computer program product, which are adapted to enhance the lifetime of electrosurgical instruments used therewith and/or enhance the safety during operation.

This object is accomplished by an electrosurgical generator as described beforehand, wherein the control unit is adapted to determine a DC-offset voltage between the two output contacts of the radiofrequency generator, check if the DC-offset voltage exceeds a DC-offset threshold value, and deactivate the ultrasonic generator if the DC-offset voltage does not exceed the DC-offset threshold value.

For the purposes of the invention, the term "deactivate" is understood to comprise a deactivation if the ultrasonic generator has been activated and/or to comprise a non-activation if the ultrasonic generator has not been activated. Therefore, the term "deactivate" can be preferably understood to comprise the deactivation of the ultrasonic generator in case it has been activated before as well as the non-activation of the ultrasonic generator in case it has not yet been activated.

The electrosurgical generator according to the present invention is based on the finding that medical devices, in particular electrosurgical instruments, which use a combination of ultrasonic vibration and radiofrequency energy have superior coagulating ability and fast cutting ability, even if comparatively low energies are used. It is currently believed that the reason for this is that the ultrasonic energy lowers the saturated vapour pressure intermittently around the ultrasonic applicator.

The invention is further based on the finding that coagulating ability is significantly enhanced if the electrosurgical instrument is combined with an additional electrically conductive tool, like a metal forceps or gripper. This additional tool is preferably used when the electrosurgical instrument does not touch the tissue but the additional tool does. The additional tool is applied touching an electrode of the electrosurgical instrument to bridge a gap between the electrode of the electrosurgical instrument and tissue to be treated, in particular coagulated. In particular, tissue interposed between the two legs of a forceps or gripper can be coagulated in an easy way when the electrically conductive forceps or gripper touches the electrode of the electrosurgical instrument. Such a mode of operation is preferred by some users since it allows to coagulate tissue in a comfortable and easy way without having to change the electrosurgical instrument. In this description, reference is made to a forceps as an additional electrically conductive tool. However, other electrically conductive additional tools are not excluded.

In this context it has been discovered by the invention that the direct contact between the electrode of the electrosurgical instrument and an additional electrically conductive tool like a forceps, while ultrasonic vibration is active, might lead to a damage of the electrosurgical instrument, for example, a damage of the ultrasonic converter.

The invention is further based on the finding that this mode of operation with an additional electrically conductive tool can be detected and controlled by monitoring a DC-offset voltage. A DC-offset voltage (DC: direct current) occurs between an electrode of the electrosurgical instrument and a further electrode if the tissue is treated without a combination with the forceps, in particular when the radiofrequency energy is activated. However, when the electrosurgical instrument is combined with the forceps, the DC-offset voltage decreases below the DC-offset threshold value. Therefore, it is determined by the control unit if the DC-offset voltage exceeds the DC-offset threshold value. If the DC-offset voltage does not exceed the DC-offset threshold value, it can be concluded that the electrosurgical instrument is used in combination with a forceps. In order to prevent damage of the electrosurgical instrument and/or the ultrasonic converter, the ultrasonic generator is deactivated so that the electrosurgical instrument is operated without ultrasonic vibration if the DC-offset voltage is below the DC-offset threshold value.

Typically, the DC-offset voltage occurs between the two potentials of the two output contacts and can be measured at any point between the radiofrequency generator and the two electrodes, e.g. the electrode of the electrosurgical instrument and the counterpart electrode. Preferably, the DC-offset voltage is measured between the two output contacts of the radiofrequency generator.

The electric currents and voltages in the system depend on the power at which the radio-frequency generator is operated, in particular the power of the radiofrequency energy provided at the two output contacts. Also, a DC-offset voltage occurring in the system depends on the power of the radiofrequency energy. Therefore, the DC-offset threshold value to be set for the control unit depends on the radiofrequency energy provided at the two output contacts. The control unit according to the present invention may detect a DC-offset voltage in a range of −200 V to +200 V, preferably in the range of −120 V to +120 V, while radiofrequency energy is activated. A preferable DC-offset threshold value lies within the range of 5V-160 V, e.g. at approximately 10V-20 V.

Therefore, according to the present invention, if the DC-offset voltage exceeds the DC-offset threshold value, the electrosurgical generator is operated with both the ultrasonic generator and the radiofrequency generator activated. If the DC-offset voltage does not exceed the DC-offset threshold value, the electrosurgical generator is operated with only the radiofrequency generator activated.

The present invention can be employed in both monopolar and bipolar applications. However, it is particularly preferred in monopolar applications with an electrosurgical instrument having only one electrode. By a monopolar application it is preferably understood that an electrode of the electrosurgical instrument is connected to one of the two output contacts at which radiofrequency energy is provided. At the same time, a counterpart electrode (also referred to as patient electrode) is connected to another one of the two output contacts at which radiofrequency energy is provided. During operation, the electrode of the electrosurgical instrument is applied to the tissue to be treated wherein the counterpart electrode is applied from the exterior of the human body, preferably in the region of the treatment zone. This means that in a monopolar arrangement the electric current flows through a large part of the body from the electrode of the electrosurgical instrument to the counterpart electrode which is generally disposed at one of the extremities. In a bipolar application, the electrosurgical instrument has two electrodes, wherein each electrode is connected to one of the two output contacts at which radiofrequency energy is provided. In such a bipolar application, the electric current flows through the tissue disposed between the two electrodes of the electrosurgical instrument. The electrosurgical instrument may have two legs, each of which having one electrode, or may be composed of one rod having two electrodes spaced apart from each other in axial direction.

The radiofrequency generator preferably comprises a radiofrequency oscillator. The radiofrequency energy is usually provided at two output contacts of the radiofrequency generator, which may be for example connected to a monopolar electrode of the electrosurgical instrument and a counterpart electrode or to a bipolar electrosurgical instrument. The high frequency alternating current generated by the radiofrequency generator may have a frequency in the range of 0.2-3 MHz.

Preferably, the ultrasonic generator comprises an ultrasonic frequency oscillator. In operation, the ultrasonic generator may generate an alternating current having a frequency of about 20-50 KHz. This excitation signal may be converted into an ultrasonic vibration by means of an ultrasonic converter. Such an ultrasonic converter is usually located in the electrosurgical instrument connected to the ultrasonic generator. In the electrosurgical instrument, the ultrasonic vibration is further transferred to an ultrasonic applicator, also called sonotrode, by means of which the ultrasonic vibration may be introduced into the tissue to be treated. The electrosurgical instrument or an applicator of the electrosurgical instrument, respectively, may be driven for example by an ultrasonic vibration which is substantially directed in axial direction of a shaft of the electrosurgical instrument or in a direction substantially perpendicular to the electrosurgical instrument shaft or on a very small circular arc section, respectively. The electrosurgical instrument can for example be utilized by a user, such that the ultrasonic vibration takes place substantially perpendicular to a tissue surface (press or push movements, respectively) or substantially parallel to a tissue surface (slide or cutting movements, respectively).

In an advantageous manner, a combined electrosurgical instrument is utilized by which the ultrasonic vibration as well as the radiofrequency energy can be introduced into the tissue. For example, the ultrasonic vibration can be used for cutting of tissue, while the radiofrequency energy can be used for coagulating the tissue to stop bleeding.

The control unit according to the present invention may be located in a housing of the electrosurgical generator or located in a separate housing being connected to units located in the electrosurgical generator housing. The control may be adapted and arranged to control the ultrasonic generator and/or the radiofrequency generator, in particular activate and deactivate the ultrasonic generator and/or the radiofrequency generator in order to activate and deactivate ultrasonic vibration and/or the radiofrequency energy at the electrosurgical instrument. The control unit may further be adapted and arranged to activate and deactive the ultrasonic vibration and/or the radiofrequency energy by operating a switch between the respective generator and the electrosurgical instrument.

In this context, deactivating the ultrasonic generator and/or the radiofrequency generator may comprise switching off the ultrasonic vibration and/or the radiofrequency energy completely. Deactivating the ultrasonic generator and/or the radiofrequency generator may further or alternatively comprise lowering the ultrasonic vibration and/or the radiofrequency energy to a very low amplitude which has no therapeutic effect, but enables the ultrasonic generator and/or the radiofrequency generator to maintain in a resonant operation. Therefore, the term "without ultrasonic vibration" is understood herein and in the following as deactivation comprising a complete shut down of the ultrasonic vibration at the electrosurgical instrument and/or a lowering of the ultrasonic vibration down to an amplitude which has no therapeutic effect, in particular no damaging effect on the electrosurgical instrument.

The control unit may have an ultrasonic control unit, which is adapted to control the ultrasonic generator, such that an excitation signal is provided by which an ultrasonic converter can generate an ultrasonic vibration. The control unit may further have a radiofrequency control unit, which is adapted to control the radiofrequency generator, such that radiofrequency energy is provided at two output contacts of the radiofrequency generator. The ultrasonic control unit and radiofrequency control unit may be separate units or an integral control unit. I.e. if the control unit is described herein, this comprises embodiments having separate units for ultrasonic control and radiofrequency control as well as one integral unit thereof, in particular also a control unit suitable for interdependent control of the radiofrequency generator and the ultrasonic generator.

According to a preferred embodiment, the electrosurgical generator comprises a spark detection unit, wherein the check if the DC-offset voltage exceeds the DC-offset threshold voltage is effected by the spark detection unit. Sparks may occur for example in a bipolar application between two electrodes of the electrosurgical instrument even in a stage where living tissue is interposed between these two distal ends. In particular after advanced coagulation, i.e. after the tissue has been interposed between the two electrodes applying radiofrequency energy for a certain amount of time, such sparks may occur. Some electrosurgical instruments are sensitive to sparks and may get damaged if sparking occurs. Therefore, it is usually desired to avoid or distinguish the spark. The termination of the spark may be initiated by a signal from the spark detection unit which detects such a spark.

Sparks may also occur when an energized electrode is removed from tissue before being de-energized. Inventors have recognized that to some extent micro-sparking continuously occurs when the electrode of an electrosurgical instrument is vibrating with ultrasonic frequency. It is currently believed that the repeated contacting and releasing of the tissue by ultrasonic vibration is responsible for this micro-sparking. According to the present invention, the spark detection unit is utilized not only for the spark detection but also for detecting if the DC-offset voltage, which occurs for example between the electrode of the electrosurgical instrument and a counterpart electrode or between two electrodes of the electrosurgical instrument, exceeds the DC-offset threshold value. This keeps the design of the electrosurgical generator simple.

In a further embodiment, the control unit is adapted to activate the ultrasonic generator prior to checking of the DC-offset voltage and deactivate the ultrasonic generator if the DC-offset voltage does not exceed the DC-offset threshold value. In general, and in particular at the beginning of a treatment procedure, the electrosurgical instrument is operated without an additional tool to cut or dissect tissue. Therefore, it is convenient to start the electrosurgical generator with both the ultrasonic and the radiofrequency generator activated. It also has to be considered that the micro-sparking responsible for occurrence of a DC-offset voltage can only occur with activated ultrasonic generator.

In a further embodiment of the electrosurgical generator, the control unit is adapted to—prior to checking if the DC-offset voltage exceeds the DC-offset threshold value— check if a radiofrequency impedance of a patient circuit exceeds an impedance threshold value, and activate the ultrasonic generator irrespective of the DC-offset voltage in case the radiofrequency impedance does not exceed the impedance threshold value. For the purposes of the invention, the patient circuit is understood to be a circuit formed by the radiofrequency generator, the electrodes of the electrosurgical instrument and, if applicable, a patient return electrode, and the patient tissue contacted by the electrodes. A high radiofrequency impedance occurs in the patient circuit if the electrosurgical instrument is not in contact with the tissue to be treated. The term "high radiofrequency impedance" is understood herein and in the following as a radiofrequency impedance which exceeds the impedance threshold value. Impedance threshold value may be between 1000 Ohm and 10.000 Ohm, preferably between 2000 Ohm and 5000 Ohm.

Cutting operation of an electrosurgical instrument is usually started with the instrument being out of contact with the tissue. After energizing the instrument it is then contacted to and moved along the tissue at the intended cutting line. For optimal results it has been found desirable that the ultrasonic generator is activated when the instrument first touches the tissue. At the same time, before the instrument touches the tissue, a DC-offset voltage cannot occur because without tissue contact no micro-sparking is possible.

A further preferred embodiment of the electrosurgical generator is characterized in that the control unit is adapted to activate the ultrasonic generator and the radiofrequency generator if the radiofrequency impedance exceeds the impedance threshold value. As described above, a high radiofrequency impedance is detected if the electrosurgical instrument does not touch the tissue to be treated. In such a situation a user usually does not combine the electrosurgical instrument with a forceps. However, the user might want to start cutting tissue. Therefore, it is important that the user is able to cut tissue smoothly at the beginning. This is achieved by the embodiment in which the ultrasonic vibration as well as the radiofrequency energy are both activated if a high radiofrequency impedance is detected.

In a further preferred embodiment, the control unit is adapted to deactivate the ultrasonic generator if the radiofrequency impedance does not exceed the impedance threshold value and the DC-offset voltage does not exceed the DC-offset threshold value. Preferably, the radiofrequency impedance is checked at first and then the DC-offset voltage is checked. After checking the radiofrequency impedance with a negative result (i.e. radiofrequency impedance does not exceed the impedance threshold value), it can be concluded that the electrosurgical instrument touches tissue or is combined with a forceps touching the tissue. Thereafter, the DC-offset voltage is checked. If both checking of the radiofrequency impedance and checking of the DC-offset voltage return a negative result, it can be concluded that the electrosurgical instrument is combined with a forceps touching the tissue. In this case the ultrasonic vibration is deactivated to reduce the risk of damage of the electrosurgical instrument.

According to a further preferred embodiment, the control unit is adapted to activate the ultrasonic generator prior to checking if the radiofrequency impedance exceeds the impedance threshold value and prior to checking if the DC-offset voltage exceeds the DC-offset threshold value; and deactivate the ultrasonic generator if the radiofrequency impedance does not exceed the impedance threshold value and the DC-offset voltage does not exceed the DC-offset threshold value. This embodiment provides for an advantageous and efficient way of operation. Especially, the cutting performance is enhanced, if the ultrasonic generator is activated immediately after starting the electrosurgical generator, in particular in the case of a user wanting to start cutting tissue to be treated right away, as is usual.

A further embodiment of the present invention is characterized in that the control unit is adapted to check for the DC-offset voltage and/or check for the radiofrequency impedance repeatedly, while both the ultrasonic generator and the radiofrequency generator are activated, preferably at each time a predetermined time interval expires. This is understood herein and in the following in a way that both checking of the DC-offset voltage and the radiofrequency impedance occurs repeatedly after regular time intervals. The dimensions of the time intervals are preferably significantly lower than the regular time dimensions of actions by the user. Preferably such a time interval is in the range of 0.1-1 seconds.

The control unit of the electrosurgical generator according to the present invention preferably is adapted to operate the electrosurgical generator as follows:

A) Starting of the electrosurgical generator, for example, in reaction to a user operating a switch of the electrosurgical generator;

B1) Activating the radiofrequency generator;

B2) Activating the ultrasonic generator;

C1) Checking if the radiofrequency impedance exceeds an impedance threshold value;
C2) If the radiofrequency impedance exceeds the impedance threshold value, checking again if the radiofrequency impedance exceeds the impedance threshold value, i.e. returning to step C1) after a predetermined time interval;
D) If the radiofrequency impedance does not exceed the impedance threshold value, checking if the DC-offset voltage exceeds a DC-offset threshold value;
E1) If the DC-offset voltage exceeds the DC-offset threshold value, checking if the radiofrequency impedance does exceed the impedance threshold value, i.e. returning to step C1) after a predetermined time interval; and
E2) Operating the electrosurgical instrument with radiofrequency energy activated and without ultrasonic vibration if the DC-offset voltage does not exceed the DC-offset threshold value.

According to a further aspect of the invention there is provided a control device for controlling an electrosurgical generator, as described above, comprising a control unit adapted to activate the radio frequency generator and activate the ultrasonic generator, wherein the control unit is further adapted to check if a DC-offset voltage exceeds a DC-offset threshold value, and deactivate the ultrasonic generator if the DC-offset voltage does not exceed the DC-offset threshold value.

According to a preferred embodiment, the control unit is coupled to a spark detection unit, wherein the spark detection unit is adapted to detect if the DC-offset voltage exceeds the DC-offset threshold value. Preferably, if the spark detection unit detects that the DC-offset voltage exceeds the DC-offset threshold value, it sends a DC-offset voltage signal to the control unit. The control unit processes this signal in order to detect if the DC-offset voltage exceeds the DC-offset threshold value.

According to a further preferred embodiment, the control unit comprises the features of the control unit described above. The control device according to the present invention and possible enhancements thereof have features which make them in particular suitable to be used for an electrosurgical generator according to the present invention. With regard to advantages, embodiments as well as embodiment details of the control device and its enhancements it is referred to the description of the respective features of the electrosurgical generator.

According to a further aspect of the invention there is provided a method for operating an electrosurgical generator having an ultrasonic generator for generating an excitation signal by which an ultrasonic converter can generate an ultrasonic vibration, and having a radiofrequency generator for providing a radiofrequency energy at two output contacts, comprising:
activating the radiofrequency generator and the ultrasonic generator;
checking if a DC-offset voltage exceeds a DC-offset threshold value; and
deactivating the ultrasonic generator if the DC-offset voltage does not exceed the DC-offset threshold value.

According to a preferred embodiment of the method, the exceeding of the DC-offset threshold value is detected by means of a spark detection unit.

A further preferred embodiment of the method comprises activating the ultrasonic generator prior to checking of DC-offset voltage and deactivating the ultrasonic generator if the DC-offset voltage does not exceed the DC-offset threshold value An even further preferred embodiment of the method comprises activating the ultrasonic generator if the DC-offset voltage exceeds the DC-offset threshold value.

In a further embodiment of the method, prior to checking if DC-offset voltage exceeds the DC-offset threshold value, it is checked if a radiofrequency impedance of a patient circuit exceeds an impedance threshold value and checking if the DC-offset voltage exceeds the DC-offset threshold value in case the radiofrequency impedance does not exceed the impedance threshold value.

An even further preferred embodiment of the method comprises operating the electrosurgical instrument with the ultrasonic vibration and the radiofrequency energy both activated if the radiofrequency impedance exceeds the impedance threshold value.

According to a further preferred embodiment, the method comprises deactivating the ultrasonic vibration if the radiofrequency impedance does not exceed the impedance threshold value and the DC-offset voltage does not exceed the DC-offset threshold value.

A further preferred embodiment of the method comprises:
activating the ultrasonic vibration prior to checking if the radiofrequency impedance exceeds the impedance threshold value and prior to checking if the DC-offset voltage exceeds the DC-offset threshold value; and
deactivating the ultrasonic vibration if the radiofrequency impedance does not exceed the impedance threshold value and the DC-offset voltage does not exceed the DC-offset threshold value.

In an even further preferred embodiment, during operation of the electrosurgical instrument with ultrasonic vibration and radiofrequency energy both activated, it is checked for the DC-offset voltage and/or checked for the radiofrequency impedance repeatedly, preferably at each time a predetermined time interval expires.

The method according to the present invention and its enhancements have features or process steps respectively, which make them in particular suitable to be used for an electrosurgical generator according to the present invention and its enhancements. With respect to the advantages, embodiments and embodiment details of the method and its enhancements it is referred to the preceding description of the respective device features.

According to a further aspect of the invention there is provided a computer program product, comprising a compressor readable medium encoded with machine-readable instructions for performing the method described above when the machine-readable instructions are run on a computer or run on the control unit described above.

BRIEF DESCRIPTION OF THE DRAWINGS

Preferred embodiments of the invention are described in an exemplary manner with reference to the attached figures, wherein

FIG. 5: illustrates a third exemplary embodiment of the method.

DETAILED DESCRIPTION

Figure 1:
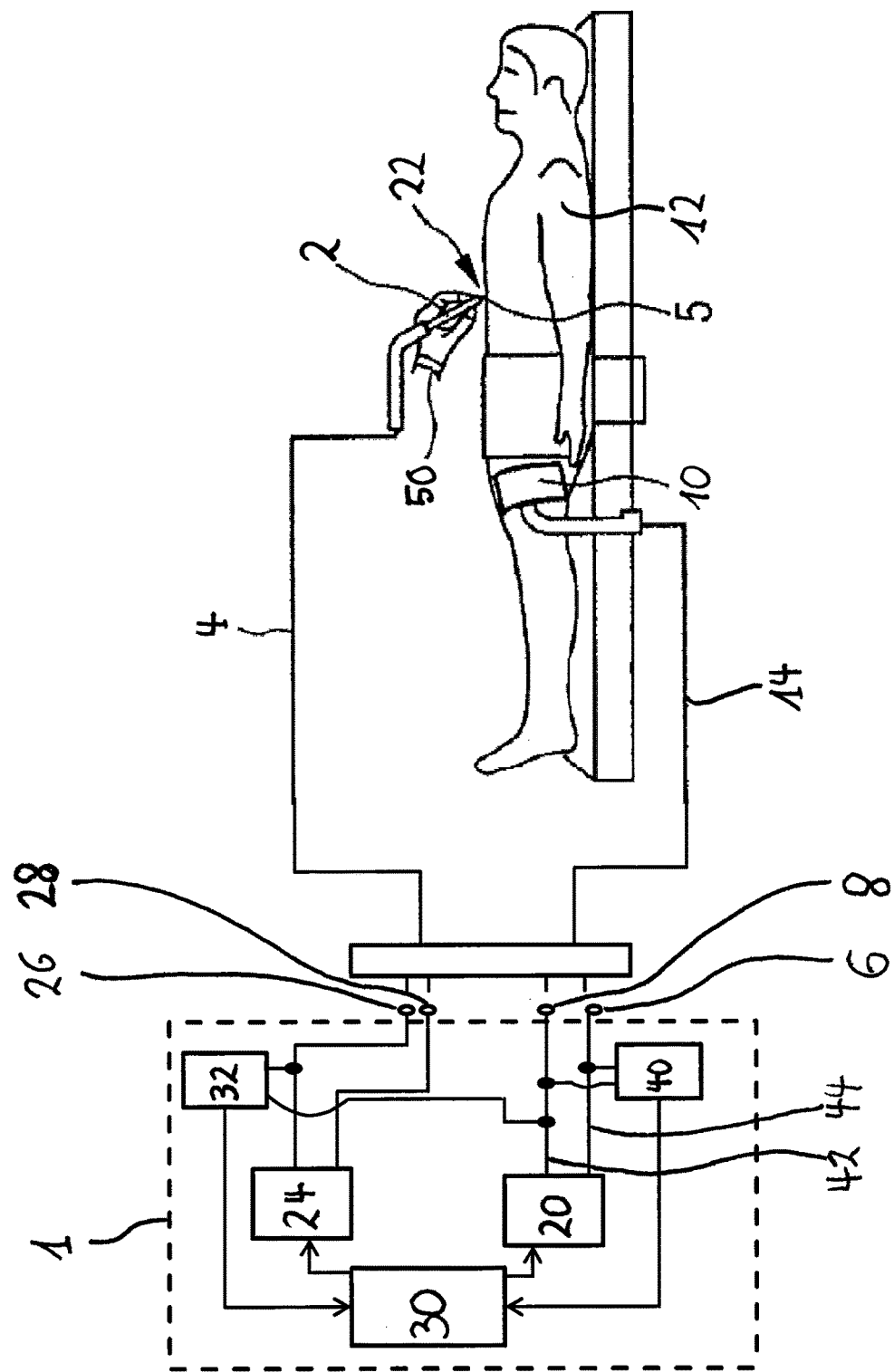
FIG. 1: illustrates a schematic illustration of an exemplary embodiment of a system having an electrosurgical generator.

An exemplary system according to the invention is shown in FIG. 1. The system comprises an electrosurgical generator 1 and an electrosurgical instrument 2. Electrosurgical instrument 2 is connected to generator 1 by means of a cable 4. The electrosurgical instrument 2 provides ultrasonic and radiofrequency treatment functionality and is used in a monopolar application. The electrosurgical instrument 2 has an electrode 5 which is coupled to one of two output contacts 6 and 8 of the generator 1. A counterpart electrode 10 is attached to an extremity (e.g. a leg) of a patient 12. The counterpart electrode 10 is to connected to generator 1 by means of a cable 14 and, thereby, coupled to another one of the output contacts 6 and 8.

The electrosurgical generator 1 comprises a radiofrequency generator 20. In operation, the radiofrequency generator 20 generates a radiofrequency energy which is provided at the two output contacts 6 and 8. Thereby, a radiofrequency circuit is formed with tissue 22 of patient 12 to be treated. This circuit is also called the patient circuit.

The electrosurgical generator 1 further comprises an ultrasonic generator 24 for providing an excitation signal for an ultrasonic vibrator (not shown) in the electrosurgical instrument 2. The vibrator and/or the electrode 5 of the electrosurgical instrument 2 are of known design and need not further be explained. The vibrator is connected to further output contacts 26 and 28 at which the excitation signal is provided.

The radiofrequency generator 20 is preferably formed by a radiofrequency oscillator and the ultrasonic generator 24 is preferably formed by an ultrasonic frequency oscillator. Main operational parameters of radiofrequency generator 20 and ultrasonic generator 24 are set by a control unit 30 based on stored operational programs and/or user input through a graphical user interface, which interface may comprise a touch-screen (not shown).

The generator 1 further comprises a detection unit 32 which is connected to the control unit 30 as well as connected to at least one output line of the ultrasonic generator 24 and the radiofrequency generator 20. The detection unit 32 uses the signals outputted by the ultrasonic generator 24 and the radiofrequency generator 20 to detect if one of the ultrasonic generator 24 and the radiofrequency generator 20 or both are active. In dependency of a detection signal received from the detection unit 32, the control unit 30 is able to activate and/or deactivate the ultrasonic generator 24 and/or the radiofrequency generator 20.

The generator 1 further comprises a spark detection unit 40 for detecting if a DC-offset voltage occurring between the electrode 5 of the electrosurgical instrument 2 and the counterpart electrode 10 exceeds a DC-offset threshold value. The spark detection unit 40 is connected to the control unit 30 as well as to the two output lines 42 and 44 of the radiofrequency generator 20. The spark detection unit 40 measures DC-offset voltage occurring between the output lines 42 and 44. If the spark detection unit 40 detects that the DC-offset voltage exceeds the DC-offset threshold value, it sends a DC-offset voltage detection signal to the control unit 30. In dependency of the DC-offset detection signal received from the spark detection unit 40, the control unit 30 is able to detect if the DC-offset voltage exceeds the DC-offset threshold value.

During operation as shown in FIG. 1, the ultrasonic generator 24 and the radiofrequency generator 20 are active. A user moves the electrode 5 of the electrosurgical instrument 2 at a cutting speed through the tissue, thereby cutting the tissue and coagulating the tissue to stop bleeding.

In case of strong bleeding, e.g. after severing a blood vessel, the user may have to stop cutting operation and stop the bleeding by enhanced coagulation, preferably including squeezing the source of bleeding using a forceps. Electrosurgical coagulation forceps are readily available, but for using such forceps the user 50 would have to connect the forceps to electrosurgical generator 1, and usually also disconnect the instrument 2. This takes additional time in which the bleeding remains uncontrolled. It has therefore been found convenient to use a standard mechanical forceps 52, which requires no connection to the generator 1. The user 50 can even keep the instrument 2 in his one hand, by taking the forceps 52 with his second hand in very short time.

Figure 2:
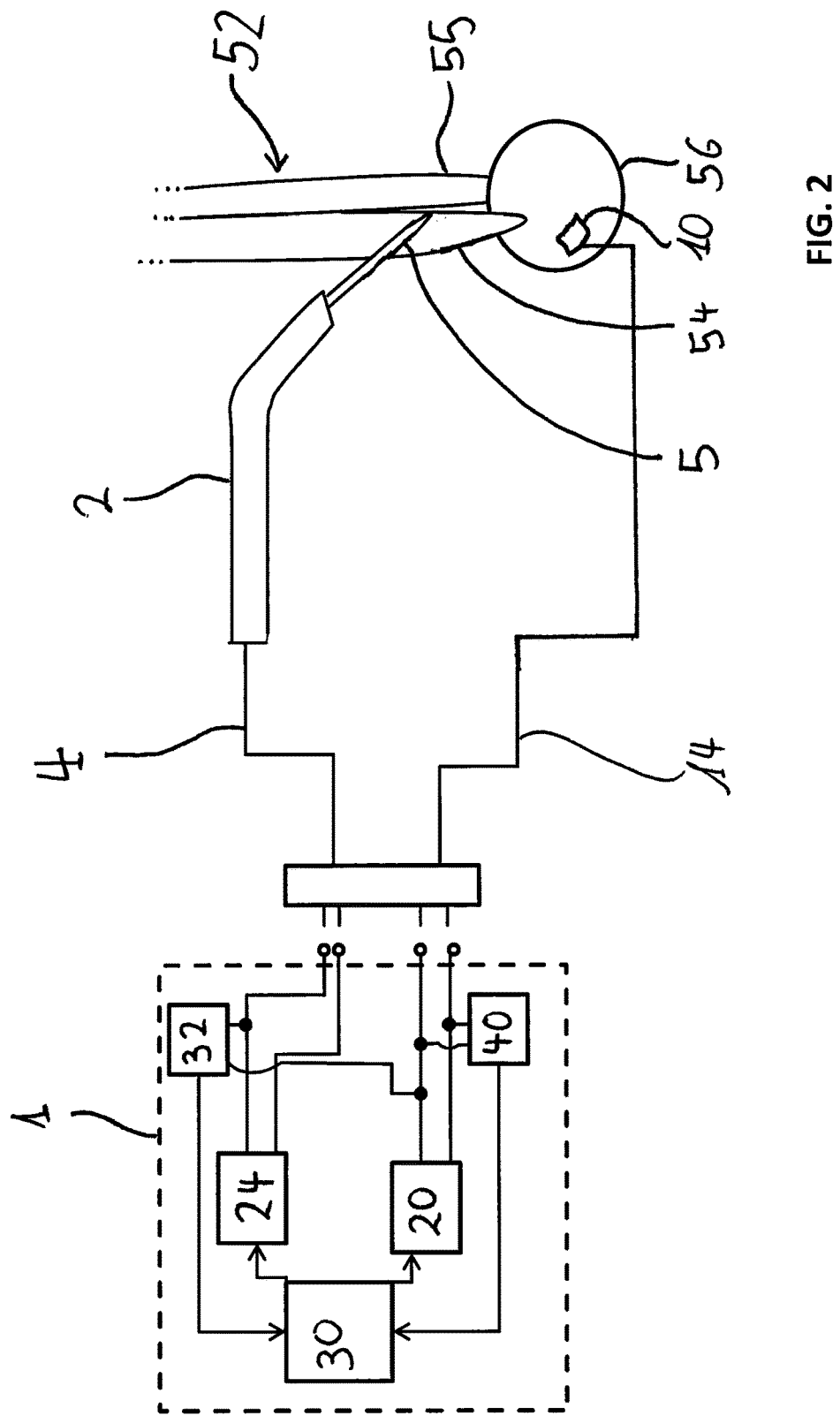
FIG. 2: illustrates the embodiment shown in FIG. 1 in another operating mode.

FIG. 2 shows schematically a mode of operation in which the user 50 combines the electrosurgical instrument 2 with a forceps 52. The user 50 combines the electrosurgical instrument 2 with the forceps 52 by contacting one leg 54 of the forceps 52 with the electrode 5 of the electrosurgical instrument 2 to enhance coagulating of tissue 56 being interposed between first leg 54 and a second leg 55 of the forceps 52.

The electrode 5 of the instrument 2, which can comprise relatively brittle material to enable ultrasonic vibration, may get damaged when contacting the leg 54 of forceps 52 while the ultrasonic vibration is active. Therefore, in this operation mode the ultrasonic generator 24 is desired to be inactive and only radiofrequency energy is provided to the electrosurgical instrument 2. However, if in this operation mode the ultrasonic generator 24 is active, it will be deactivated by the control unit 30 after the control unit 30 detects that the DC-offset voltage does not exceed the DC-offset threshold value. In this case, the electrosurgical generator 1 will be operated only with radiofrequency energy.

Preferred exemplary embodiments of the method according to the present invention and the control logic implemented in the control unit for operating the described system, in particular the electrosurgical generator 1, are explained below with reference to FIGS. 3-5. In the following description, reference is made to the occurrence or detection of a "high radiofrequency impedance" which is understood herein and in the following as a radiofrequency impedance of the patient circuit exceeding an impedance threshold value. Additionally in the following description, it is made reference to the occurrence or detection of "a DC-offset voltage" which is understood herein and in the following as a DC-offset voltage exceeding a DC-offset threshold value.

Figure 3:
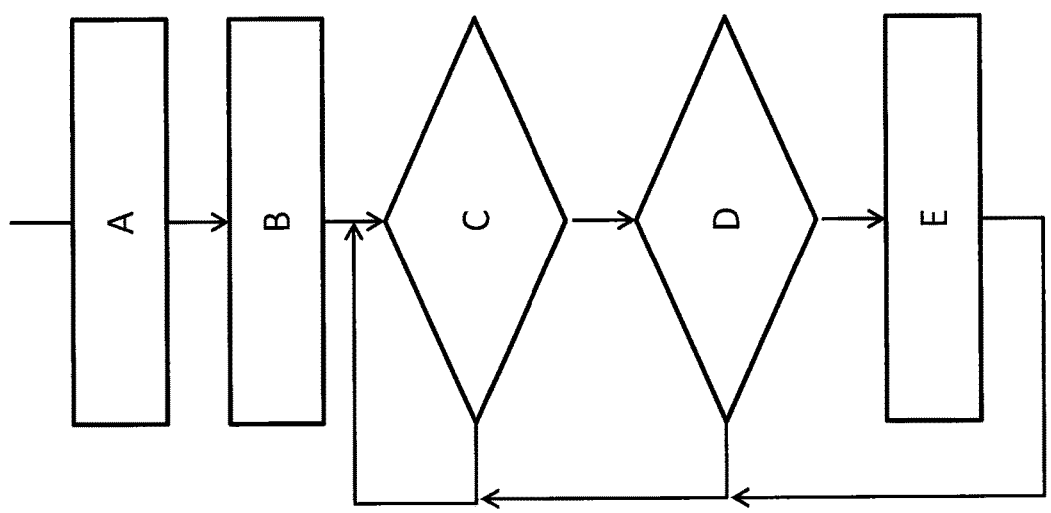
FIG. 3: illustrates a first exemplary embodiment of a method according to the present invention.

FIG. 3 shows a flow chart schematically illustrating an exemplary process of operating the electrosurgical generator 1 shown in FIG. 1.

In a first process step A, the electrosurgical generator 1 is started by the user 50 operating an electro-mechanical switch or a button of the graphical user interface.

In a second process step B, the control unit 30 activates the ultrasonic generator 24 as well as the radiofrequency generator 20.

In a subsequent process step C, the control unit 30 checks if a high radiofrequency impedance occurs, e.g. between the electrode 5 of the electrosurgical instrument 2 and the counterpart electrode 10.

If a high radiofrequency impedance is detected by the control unit 30, the electrosurgical generator 1 stands by for a predetermined amount of time, after which step C is repeated, i.e. it is checked if a high radiofrequency impedance occurs.

If no high radiofrequency impedance is detected, the control unit 30 checks in a process step D if a DC-offset voltage occurs between the electrode 5 of the electrosurgical instrument 2 and the counterpart electrode 10. If a DC-offset voltage is detected, the control unit 30 returns to step C, i.e. the control unit 30 checks if a high radiofrequency impedance occurs. If no DC-offset voltage is detected, the control unit 30, in a process step E, deactivates the ultrasonic generator 24 and keeps the radiofrequency generator 20 active. After executing process step E, the control unit 30 stands by for a predetermined amount of time to return to step C. The predetermined amount of time will usually be quite short, e.g. between 0.1 and 1 second, to facilitate quasi-continuous cycling of the control algorithm described above.

Figure 4:
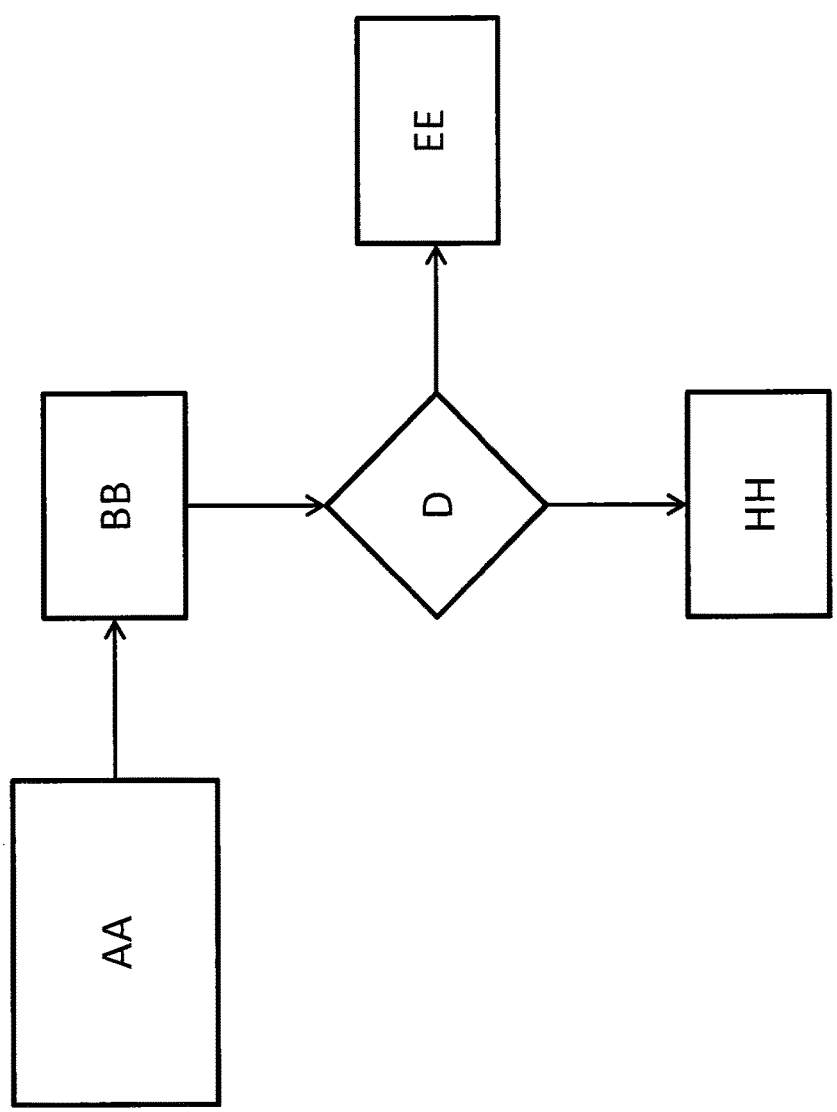
FIG. 4: illustrates a second exemplary embodiment of the method.

FIG. 4 shows a second flow chart illustrating a second embodiment of a method for operating the electrosurgical generator 1 shown in FIG. 1. The method illustrated in FIG. 4 is similar to the method illustrated in FIG. 3. The same and similar features are indicated by the same reference numerals.

In a first process step AA, the electrosurgical generator 1 is started. In a second process step BB, the control unit 30 activates the radiofrequency generator 20 so that radiofrequency energy is provided at the electrode 5 of the electrosurgical instrument 2. In a further process step D, the control unit 30 checks if a DC-offset voltage occurs.

If no DC-offset voltage is detected in process step D, the control unit 30 proceeds to process step EE, in which the radiofrequency generator is kept active while the ultrasonic generator 24 is kept inactive. In such a situation, the user 50 is able to apply the electrosurgical instrument 2 combined with a forceps for coagulating of tissue.

If a DC-offset voltage is detected in process step D, the control unit 30 proceeds to process step HH, in which the ultrasonic generator is activated. Furthermore, the control unit 30 keeps the radiofrequency generator 20 in an active state. In this situation, the user 50 may use the electrosurgical instrument for dissection of tissue.

FIG. 5 shows a flow chart schematically illustrating a third embodiment of a method for operating the electrosurgical generator 1 shown in FIG. 1. The method illustrated in FIG. 5 is similar to the methods illustrated in FIGS. 2 and 3. The same and similar features are indicated by the same reference numerals.

After the electrosurgical generator 1 has been started by the user 50, the control unit 30 activates the radiofrequency generator 20 in a first process step BBB. In a second process step CCC, the control unit 30 checks if a high radiofrequency impedance occurs.

If in process step CCC, a high radiofrequency impedance is detected, the control unit 30 activates the ultrasonic generator 24 in a process step G.

If in process step CCC, the control unit 30 does not detect a high radiofrequency impedance, the control unit 30 executes a process step DDD, in which it checks if a DC-offset voltage occurs. If in step DDD control unit 30 does not detect a DC-offset voltage, it proceeds to process step EEE, in which the radiofrequency generator 20 is kept active while the ultrasonic generator 24 is kept inactive. If in process step DDD the control unit 30 does detect a DC-offset voltage, it proceeds to process step G.

According to the invention and the exemplary embodiments shown in the drawings, it is automatically detected whether or not the user operates the electrosurgical generator with electrosurgical instrument alone or together with an additional electrically conductive tool contacting the electrode of the electrosurgical instrument bridging a gap between the electrosurgical instrument and the tissue. The supply of ultrasonic and radiofrequency energy is adopted to the result of this detection such that the generator does not provide ultrasonic energy to the electrosurgical instrument in case it is used with the additional tool to prevent damage to the electrosurgical instrument. Therefore, a user can simply operate an electrosurgical instrument coupled to the electrosurgical generator in a desired way to realize the desired functionality without actively having to change instruments or settings of the electrosurgical generator.

REFERENCE NUMERALS 1 electrosurgical generator
2 electrosurgical instrument
4 cable
5 electrode
6, 8 output contact
10 counterpart electrode
12 patient
14 cable
20 radiofrequency generator
22 tissue
24 ultrasonic generator
26, 28 output contact
30 control unit
32 detection unit
40 spark detection unit
42, 44 output lines
50 user
52 forceps
54, 55 leg
56 tissue
A-G process step
AA, BB, EE, HH process step
BBB, CCC, DDD, EEE process step

The invention claimed is:
1. An electrosurgical generator, comprising:
an ultrasonic generator for providing an excitation signal by which an ultrasonic converter can generate an ultrasonic vibration;
a radiofrequency generator for providing a radiofrequency energy at two output contacts; and
a control unit adapted to independently activate the radiofrequency generator and the ultrasonic generator,
wherein the control unit is adapted to:
determine a DC-offset voltage between the two output contacts of the radiofrequency generator;
check if the DC-offset voltage exceeds a DC-offset threshold value; and
deactivate the ultrasonic generator if the DC-offset voltage does not exceed the DC-offset threshold value.
2. The electrosurgical generator according to claim 1, further comprising a spark detection unit, wherein the check if the DC-offset voltage exceeds the DC-offset threshold voltage is effected by the spark detection unit.
3. The electrosurgical generator according to claim 1, wherein the control unit is adapted to activate the ultrasonic generator prior to checking of the DC-offset voltage and deactivate the ultrasonic generator if the DC-offset voltage does not exceed the DC-offset threshold value.

4. The electrosurgical generator according to claim 1, wherein the control unit is adapted to:
   prior to checking if the DC-offset voltage exceeds the DC-offset threshold value, check if a radiofrequency impedance of a patient circuit exceeds an impedance threshold value; and
   activate the ultrasonic generator irrespective of the DC-offset voltage in case the radiofrequency impedance exceeds the impedance threshold value.

5. The electrosurgical generator according to claim 4, wherein the control unit is adapted to activate the ultrasonic generator and the radiofrequency generator if the radiofrequency impedance exceeds the impedance threshold value.

6. The electrosurgical generator according to claim 1, wherein the control unit is adapted to deactivate the ultrasonic generator if a radiofrequency impedance does not exceed an impedance threshold value and the DC-offset voltage does not exceed the DC-offset threshold value.

7. The electrosurgical generator according to claim 1, wherein the control unit is adapted to:
   activate the ultrasonic generator prior to checking if a radiofrequency impedance exceeds an impedance threshold value and prior to checking if the DC-offset voltage exceeds the DC-offset threshold value; and
   deactivate the ultrasonic generator if the radiofrequency impedance does not exceed the impedance threshold value and the DC-offset voltage does not exceed the DC-offset threshold value.

8. The electrosurgical generator according to claim 1, wherein the control unit is adapted to check for the DC-offset voltage and/or check for a radiofrequency impedance repeatedly, while both the ultrasonic generator and the radiofrequency generator are activated.

9. A control device for controlling an electrosurgical generator comprising:
   an ultrasonic generator for providing an excitation signal by which an ultrasonic converter can generate an ultrasonic vibration;
   a radiofrequency generator for providing a radiofrequency energy at two output contacts; and
   a control unit adapted to:
      activate the radiofrequency generator and activate the ultrasonic generator, wherein the control unit is adapted to:
         check if a DC-offset voltage exceeds a DC-offset threshold value; and
         deactivate the ultrasonic generator if the DC-offset voltage does not exceed the DC-offset threshold value.

10. The control device according to claim 9, wherein the control unit is adapted to:
   activate the ultrasonic generator prior to checking of the DC-offset voltage and deactivate the ultrasonic generator if the DC-offset voltage does not exceed the DC-offset threshold value,
   prior to checking if the DC-offset voltage exceeds the DC-offset threshold value, check if a radiofrequency impedance of a patient circuit exceeds an impedance threshold value,
   activate the ultrasonic generator irrespective of the DC-offset voltage in case the radiofrequency impedance exceeds the impedance threshold value,
   activate the ultrasonic generator and the radiofrequency generator if the radiofrequency impedance exceeds the impedance threshold value,
   activate the ultrasonic generator prior to checking if the radiofrequency impedance exceeds the impedance threshold value and prior to checking if the DC-offset voltage exceeds the DC-offset threshold value,
   deactivate the ultrasonic generator if the radiofrequency impedance does not exceed the impedance threshold value and the DC-offset voltage does not exceed the DC-offset threshold value, and
   check for the DC-offset voltage and/or check for the radiofrequency impedance repeatedly, while both the ultrasonic generator and the radiofrequency generator are activated.

11. A method for operating an electrosurgical generator having an ultrasonic generator for generating an excitation signal by which an ultrasonic converter can generate an ultrasonic vibration, and having a radiofrequency generator for providing a radiofrequency energy at two output contacts, comprising:
   activating the radiofrequency generator and the ultrasonic generator;
   checking if a DC-offset voltage exceeds a DC-offset threshold value; and
   deactivating the ultrasonic generator if the DC-offset voltage does not exceed the DC-offset threshold value.

12. The method according to claim 11, comprising:
   prior to checking if the DC-offset voltage exceeds the DC-offset threshold value, checking if a radiofrequency impedance of a patient circuit exceeds an impedance threshold value; and
   checking if the DC-offset voltage exceeds the DC-offset threshold value in case the radiofrequency impedance does not exceed the impedance threshold value.

13. A non-transitory computer-readable storage medium storing a program to execute the method according to claim 12, and the following steps:
   determine a DC-offset voltage between the two output contacts of the radiofrequency generator:
   check if the DC-offset voltage exceeds a DC-offset threshold value; and
   deactivate the ultrasonic generator if the DC-offset voltage does not exceed the DC-offset threshold value.

* * * * *